(12) United States Patent
Barrow-Williams et al.

(10) Patent No.: US 9,427,525 B2
(45) Date of Patent: Aug. 30, 2016

(54) AUTO-INJECTOR

(75) Inventors: Timothy Donald Barrow-Williams, Herts (GB); Matthew Ekman, Cheshire (GB)

(73) Assignee: Sanofi-Aventis Deutschland GMBH, Franfurt am Main (DE)

( * ) Notice: Subject to any disclaimer, the term of this patent is extended or adjusted under 35 U.S.C. 154(b) by 709 days.

(21) Appl. No.: 13/993,526

(22) PCT Filed: Dec. 21, 2011

(86) PCT No.: PCT/EP2011/073501
§ 371 (c)(1),
(2), (4) Date: Jun. 12, 2013

(87) PCT Pub. No.: WO2012/085020
PCT Pub. Date: Jun. 28, 2012

(65) Prior Publication Data
US 2013/0274668 A1 Oct. 17, 2013

(30) Foreign Application Priority Data
Dec. 21, 2010 (EP) .................................... 10196066

(51) Int. Cl.
*A61M 5/20* (2006.01)
*A61M 5/32* (2006.01)

(52) U.S. Cl.
CPC ............. *A61M 5/20* (2013.01); *A61M 5/2033* (2013.01); *A61M 5/3202* (2013.01); *A61M 5/326* (2013.01);
(Continued)

(58) Field of Classification Search
None
See application file for complete search history.

(56) References Cited

U.S. PATENT DOCUMENTS

| 5,480,387 | A | * | 1/1996 | Gabriel | .................... | A61M 5/20 |
| | | | | | | 604/134 |
| 5,599,309 | A | * | 2/1997 | Marshall | ............. | A61M 5/2033 |
| | | | | | | 604/117 |

(Continued)

FOREIGN PATENT DOCUMENTS

| EP | 1728529 | 12/2006 |
| WO | 2009/037141 | 3/2009 |

(Continued)

OTHER PUBLICATIONS

International Search Report for Int. App. No. PCT/EP2011/073501, completed Mar. 2, 2012.

*Primary Examiner* — Kevin C Sirmons
*Assistant Examiner* — William Carpenter
(74) *Attorney, Agent, or Firm* — Fish & Richardson P.C.

(57) ABSTRACT

The invention refers to an auto-injector comprising:
  a body, a syringe with a hollow injection needle and a stopper, wherein the syringe is slidably arranged with respect to the body,
  a torsion spring capable of, upon activation:
  pushing the needle from a covered position inside the body into an advanced position through the orifice and past the proximal end (P),
  operating the syringe to supply the dose of medicament (M), and
  activating means arranged to lock the spring means in a pressurized state prior to manual operation and capable of, upon manual operation, releasing the spring means for injection,
  wherein the torsion spring is grounded at one end in the body and at the other end in a first gear member rotatable about a longitudinal axis, wherein the first gear member, upon rotation, is arranged for translating a second gear member toward the proximal end (P), the second gear member prevented from rotating and arranged to be coupled to the stopper in order to push it towards the proximal end (P), wherein the first gear member is engaged with the activating means prior to manual operation in a manner to prevent rotation and disengaged from the activating means upon manual operation,
  characterized in that a ratchet wheel is arranged on the first gear member, the ratchet wheel having a number of circumferentially arranged teeth, wherein the activating means comprise at least one locking feature for engaging the ratchet wheel in a manner to prevent rotation and wherein the locking feature is arranged to allow rotation on manual operation.

15 Claims, 11 Drawing Sheets

(52) U.S. Cl.
CPC .. *A61M 2005/206* (2013.01); *A61M 2005/208* (2013.01); *A61M 2005/2013* (2013.01); *A61M 2005/2086* (2013.01)

(56) References Cited

U.S. PATENT DOCUMENTS

| | | | | |
|---|---|---|---|---|
| 8,808,250 | B2* | 8/2014 | Ekman | A61M 5/2033 604/136 |
| 9,227,016 | B2* | 1/2016 | Ekman | A61M 5/2033 |
| 2002/0095120 | A1 | 7/2002 | Larsen et al. | |
| 2005/0261634 | A1* | 11/2005 | Karlsson | A61M 5/20 604/197 |
| 2006/0234298 | A1* | 10/2006 | Chiu | B01L 3/5025 435/7.1 |
| 2006/0287630 | A1 | 12/2006 | Hommann | |
| 2009/0088688 | A1* | 4/2009 | Barrow-Williams | A61M 5/2033 604/136 |
| 2010/0280460 | A1* | 11/2010 | Markussen | A61M 5/2033 604/195 |
| 2010/0324485 | A1* | 12/2010 | Cowe | A61M 5/20 604/134 |
| 2011/0106008 | A1* | 5/2011 | Kronestedt | A61M 5/2033 604/110 |

FOREIGN PATENT DOCUMENTS

| | | |
|---|---|---|
| WO | 2009/081133 | 7/2009 |
| WO | 2009/098502 | 8/2009 |

* cited by examiner

AUTO-INJECTOR

CROSS REFERENCE TO RELATED APPLICATIONS

The present application is a U.S. National Phase Application pursuant to 35 U.S.C. §371 of International Application No. PCT/EP2011/073501 filed Dec. 21, 2011, which claims priority to European Patent Application No. 10196066.4 filed Dec. 21, 2010. The entire disclosure contents of these applications are herewith incorporated by reference into the present application.

TECHNICAL FIELD

The invention relates to an auto-injector for administering a dose of a liquid medicament according to the preamble of claim 1.

BACKGROUND

Administering an injection is a process which presents a number of risks and challenges for users and healthcare professionals, both mental and physical.

Injection devices (i.e. devices capable of delivering medicaments from a medication container) typically fall into two categories—manual devices and auto-injectors.

In a manual device—the user must provide the mechanical energy to drive the fluid through the needle. This is typically done by some form of button/plunger that has to be continuously pressed by the user during the injection. There are numerous disadvantages to the user from this approach. If the user stops pressing the button/plunger then the injection will also stop. This means that the user can deliver an under dose if the device is not used properly (i.e. the plunger is not fully pressed to its end position). Injection forces may be too high for the user, in particular if the patient is elderly or has dexterity problems.

The extension of the button/plunger may be too great. Thus it can be inconvenient for the user to reach a fully extended button. The combination of injection force and button extension can cause trembling/shaking of the hand which in turn increases discomfort as the inserted needle moves.

Auto-injector devices aim to make self-administration of injected therapies easier for patients. Current therapies delivered by means of self-administered injections include drugs for diabetes (both insulin and newer GLP-1 class drugs), migraine, hormone therapies, anticoagulants etc.

Auto-injectors are devices which completely or partially replace activities involved in parenteral drug delivery from standard syringes. These activities may include removal of a protective syringe cap, insertion of a needle into a patient's skin, injection of the medicament, removal of the needle, shielding of the needle and preventing reuse of the device. This overcomes many of the disadvantages of manual devices. Injection forces/button extension, hand-shaking and the likelihood of delivering an incomplete dose are reduced. Triggering may be performed by numerous means, for example a trigger button or the action of the needle reaching its injection depth. In some devices the energy to deliver the fluid is provided by a spring.

US 2002/0095120 A1 discloses an automatic injection device which automatically injects a pre-measured quantity of fluid medicine when a tension spring is released. The tension spring moves an ampoule and the injection needle from a storage position to a deployed position when it is released. The content of the ampoule is thereafter expelled by the tension spring forcing a piston forward inside the ampoule. After the fluid medicine has been injected, torsion stored in the tension spring is released and the injection needle is automatically retracted back to its original storage position.

The post published PCT/EP2010/066313 discloses an auto-injector for administering a dose of a liquid medicament, comprising:

an elongate outer casing arranged to contain a syringe with a hollow needle and a stopper for sealing the syringe and displacing the medicament, the outer casing having a distal end and a proximal end with an orifice intended to be applied against an injection site, wherein the syringe is slidably arranged with respect to the outer casing, spring means capable of, upon activation:

pushing the needle from a covered position inside the outer casing into an advanced position through the orifice and past the proximal end, operating the syringe to supply the dose of medicament, and retracting the syringe with the needle into the covered position after delivering the medicament, activating means arranged to lock the spring means in a pressurized state prior to manual operation and capable of, upon manual operation, releasing the spring means for injection. The spring means is a torsion spring grounded at one end in the outer casing and at the other end in a first gear member rotatable about a longitudinal axis, wherein the first gear member, upon rotation, is arranged for translatively moving a second gear member toward the proximal end, the second gear member prevented from rotating and coupled to the stopper in order to push it towards the proximal end, wherein the first gear member is engaged with the activating means prior to manual operation in a manner to prevent rotation and disengaged from the activating means upon manual operation.

SUMMARY

It is an object of the present invention to provide an improved auto-injector.

The object is achieved by an auto-injector according to claim 1.

Preferred embodiments of the invention are given in the dependent claims.

In the context of this specification the term proximal refers to the direction pointing towards the patient during an injection while the term distal refers to the opposite direction pointing away from the patient.

According to the invention an auto-injector for administering a dose of a liquid medicament comprises:

a body arranged to contain a syringe with a hollow injection needle and a stopper for sealing the syringe and displacing the medicament, the body having a distal end and a proximal end with an orifice intended to be applied against an injection site, wherein the syringe is slidably arranged with respect to the body, a torsion spring capable of, upon activation:

pushing the needle from a covered position inside the body into an advanced position through the orifice and past the proximal end, operating the syringe to supply the dose of medicament, and activating means arranged to lock the spring means in a pressurized state prior to manual operation and capable of, upon manual operation, releasing the spring means for injection.

The torsion spring is grounded at one end in the body and at the other end in a first gear member rotatable about a longitudinal axis, wherein the first gear member, upon rotation, is arranged for translating a second gear member toward the proximal end, the second gear member prevented from rotating and arranged to be coupled to the stopper in order to push it towards the proximal end, wherein the first gear member is engaged with the activating means prior to manual operation in a manner to prevent rotation and disengaged from the activating means upon manual operation.

The single torsion spring is used for inserting the needle and fully emptying the syringe. It may also be arranged for retracting the syringe and needle to a safe position after injection or for advancing a needle shroud over the needle for covering it. A major advantage of the torsion spring with the gear arrangement is that force is exerted on the stopper and syringe in a smooth manner, whereas a conventional compression spring exhibits a rather abrupt force deployment which may spoil a glass syringe or other parts of the auto-injector.

According to the invention a ratchet wheel is arranged on the first gear member, the ratchet wheel having a number of circumferentially arranged teeth. The activating means comprise at least one locking feature for engaging the ratchet wheel in a manner to prevent rotation. The locking feature is arranged to allow rotation on manual operation of the activating means. Controlling the torsion spring through the ratchet wheel is a particularly simple and efficient solution. The ratchet mechanism may be arranged to allow reengagement in order to interrupt and restart the injection.

In one embodiment the activating means may comprise a wrap-over trigger sleeve arranged over the distal end of the auto-injector and translatable between a distal position and a proximal position. The trigger sleeve is biased in distal direction. The locking feature is at least one resilient cantilever clip arranged on the body in a position to be forced outward by the ramped teeth of the rotating ratchet wheel with their ramps pointing towards a direction of rotation of the first gear member, wherein the trigger sleeve comprises at least one stop for outwardly supporting the cantilever clip when the trigger sleeve is in the distal position. The stop is arranged to be removed from behind the cantilever clip on translation of the trigger sleeve into the proximal position.

In order to trigger an injection the auto-injector has to be pressed against an injection site, e.g. a patient's skin. A user, e.g. the patient or a caregiver, grabs the wrap-over sleeve button with their whole hand and pushes against the injection site. Consequently, the trigger button translates in proximal direction and releases the drive spring for starting the injection cycle. This embodiment is particularly well suited for people with dexterity problems since, as opposed to conventional art auto-injectors, triggering does not require operation of small buttons by single fingers. Instead, the whole hand is used. Furthermore, this embodiment provides an audible and tactile feedback that the injection is in progress by the cantilever clip running over the teeth of the ratchet wheel.

In another embodiment the activating means comprises a trigger button laterally arranged on the body and pivoted about a trigger pivot in the body. The locking feature is a tooth arranged on the trigger button. The tooth is engaged with the ratchet wheel in an initial state prior to actuation of the trigger button. The tooth is arranged to be moved outwards and disengaged from the ratchet wheel on actuation of the trigger button. A lateral trigger button can be easier to operate for people with dexterity problems compared to auto-injectors with trigger buttons arranged at the distal end.

An interlock sleeve may be arranged in the proximal part of the body in a manner to protrude from the proximal end in the initial state under bias of an interlock spring. The interlock sleeve is translatable in distal direction into a distal position against the load of the interlock spring by pushing the proximal end against the injection site. A catch is arranged on the interlock sleeve in a manner to engage a catch on the trigger button so as to prevent the trigger button from being operated when the interlock sleeve is in the proximal position. The catches are arranged to be disengaged on translation of the interlock sleeve into the distal position. Hence, translation of the interlock sleeve unlocks the trigger button so as to allow actuation.

This results in an auto-injector with a sequenced operation. In the as delivered initial state the interlock sleeve is in its proximal position protruding from the proximal end of the body. The syringe and needle are in their retracted position. In order to trigger an injection the auto-injector has to be pressed with its proximal end against the injection site in a manner to translate the interlock sleeve in distal direction into the body. This translation allows the trigger button to be actuated for eventually releasing the drive spring and start an injection cycle. The probability for inadvertent operation of the auto-injector decreases due to the requirement of two sequenced user actions, pressing the auto-injector against the injection site and operating the trigger button.

The trigger button may be biased towards the position in the initial state so as to allow the tooth on the trigger button to reengage the ratchet wheel for interrupting rotation of the first gear member and hence interrupting the injection.

In this case the ratchet wheel may comprise circumferentially arranged ramped teeth with their ramps pointing against a direction of rotation of the first gear member. Thus, reengagement of the tooth on the trigger button with the ratchet wheel is facilitated.

The first gear member may be coupled to a retraction slider tube for joint translative movement but independent rotation. The retraction slider tube may be arranged in a proximal part of the outer casing in a manner to be prevented from rotation, e.g. by one or more flats or splines guided in correspondent flats or splines in the outer casing. Furthermore latches for preventing the retraction slider tube from being axially moved are provided in the outer casing. The latches are engaged for the most part of the operation of the auto-injector, i.e. before and during needle insertion and injection. When the second gear member is advanced into or near a maximum proximal position at the end of the injection the latches are disengaged by ramp features of the second gear member pushing the latches outward thus releasing the retraction slider tube for being translatively moved in distal direction. As long as the latches are engaged the second gear member is forced in proximal direction by the axially fixed and rotating first gear member. When the latches are disengaged the second gear member has at least nearly reached the end of its travel and bottomed out at the proximal end of the outer casing. Due to the disengaged latches the first gear member and the retraction slider tube are now pulled in distal direction by continued rotation of the torsion spring and the first gear member since the second gear member cannot advance further. The retraction slider tube comprises at least one dog feature for taking along the syringe carrier with the syringe when the retraction slider tube is retracted. The syringe carrier is retracted into the auto-injector until the hollow needle is fully covered. The dog feature preferably extends inwardly from the refraction slider tube through recesses in the second gear member.

The first and second gear members may be in the shape of tubes telescoped into each other. The first gear member may be a follower tube and the second gear member a lead screw tube, with the lead screw tube telescoped into the follower tube. The lead screw tube has a lead screw thread engaged with the follower tube by at least one ball bearing. The lead screw thread may be a multi start thread each one engaged to the follower tube by a respective ball. In an alternative embodiment the follower tube may be engaged with the lead screw by a pin. However, the ball bearing is preferred in order to achieve a low friction contact.

For the purposes of clarity, from hereon in the following description of operation of the device, the first gear member will be referred to as the 'follower tube' and the second gear member will be referred to as the 'lead screw tube'

The syringe may be held in an essentially tubular syringe carrier and supported at its proximal end therein, wherein the syringe carrier is slidably arranged in the lead screw tube. Supporting the syringe at its proximal end rather than at its flanges avoids damaging the syringe under load since the flanges are more fragile, in particular in a glass syringe.

In order to insert the hollow needle and to inject the dose the lead screw tube may be coupled to the stopper by a plunger which is releasably engageable with the lead screw tube for joint axial movement. The plunger is disengageable from the lead screw tube upon the lead screw tube reaching its maximum proximal position in order to allow the syringe to be retracted after injection.

In one embodiment the plunger is engageable with the lead screw tube by at least one plunger ball detent. The detent ball may be held in a recess in the lead screw tube and engage a circumferential notch in the plunger. In order to stay engaged with the notch the ball is supported by the follower tube until the lead screw tube reaches the end of its travel. At this point the detent ball reaches a pocket in the follower tube so it is no longer supported and the detent ball drops into the pocket thus disengaging the plunger from the lead screw tube.

The plunger may comprise a plunger rear and a plunger front telescoped into each other. A plunger spring is arranged between the plunger rear and plunger front. The plunger spring may be a compression spring or a piece of resilient material such as plastic or rubber foam or a pneumatic spring. It is arranged for being partially compressed when the plunger is advanced to push the stopper towards the proximal end. This partial compression happens due to friction between the stopper and the inner wall of the syringe and due to hydraulic resistance of the liquid medicament forced through the small fluid channel in the hollow needle.

The lead screw tube may be provided with pockets containing a viscous damper at the proximal end of the lead screw tube. The viscous damper is arranged for being compressed by a rib arranged in the proximal end of the outer casing when the lead screw tube nearly reaches its maximum proximal position. Thereby part of the load from the lead screw tube is resolved and the plunger spring is allowed to expand. Thus the stopper is advanced further by the compression spring so residual medicament is expelled from the syringe. This allows for dealing with the problem that the syringe and stopper are subject to large tolerances making it virtually impossible to expel the whole content of the syringe and trigger the retraction of the syringe exactly at the end of the injection. With conventional auto-injectors the stopper will either bottom out before the retraction can be triggered, (thus the syringe is emptied but the syringe and needle are never retracted so the risk for needlestick injuries is tremendously increased), or the retraction will be triggered before the stopper bottoms out in the syringe. In this case the syringe and needle are indeed retracted to a safe position but the syringe is not fully emptied.

The auto-injector with the viscous damper and the plunger spring allows for solving both problems, reliably retracting the hollow needle to a safe position and fully emptying the syringe which is particularly desirable with expensive drugs. Emptying the syringe is also important for dosage accuracy.

When the stopper has nearly reached the end of its travel the viscous damper contacts ribs in the proximal end of the outer casing. A velocity dependent load opposes the motion of the lead screw tube slowing it down. As a result load on the plunger is reduced due to the reduced hydraulic resistance of the flow of medicament passing through the hollow needle. This allows the plunger spring to expand and empty the residual dose of medicament. The lead screw tube is further advanced until it bottoms out in the proximal end of the outer casing. Shortly before this the ramp features disengage the latches so the retraction slider tube can be moved in the distal direction taking with it the syringe carrier and syringe as soon as the plunger and the lead screw tube are decoupled by the detent ball falling into the pocket. Thus the stopper is kept from stalling the retraction and the syringe is fully emptied.

The follower tube and the retraction slider tube preferably exhibit respective circumferential shoulders facing each other and held together by a coupling ring. This allows for independent rotation while joint axial movement is ensured.

In a preferred embodiment the lead screw thread has a variable pitch arranged in a manner to advance the lead screw tube faster and with less force when inserting the hollow needle (steep pitch) and more slowly with increased force when expelling the medicament (flat pitch). At the end of the travel of the lead screw tube the pitch is preferably even flatter in order to increase the force for compressing the viscous damper. A rapid needle insertion is known to reduce pain felt by the patient. A variable pitch also allows a steady delivery of the dose. The repeatability of the time required for the operational cycle of the auto-injector is important to the user. If the time required is highly variable between devices then the user may be confused and make errors in delivering the injection. Changing the pressure angle of the lead screw or cam track allows the load from the spring to be applied either more or less directly to the plunger, e.g. if there is a step in the device cycle that requires a high axial load such as when compressing the viscous damper or operating the latches for triggering the needle retraction.

Further scope of applicability of the present invention will become apparent from the detailed description given hereinafter. However, it should be understood that the detailed description and specific examples, while indicating preferred embodiments of the invention, are given by way of illustration only, since various changes and modifications within the spirit and scope of the invention will become apparent to those skilled in the art from this detailed description.

BRIEF DESCRIPTION OF THE DRAWINGS

The present invention will become more fully understood from the detailed description given hereinbelow and the accompanying drawings which are given by way of illustration only, and thus, are not limitive of the present invention, and wherein.

Corresponding parts are marked with the same reference symbols in all figures.

DETAILED DESCRIPTION

Figure 1:
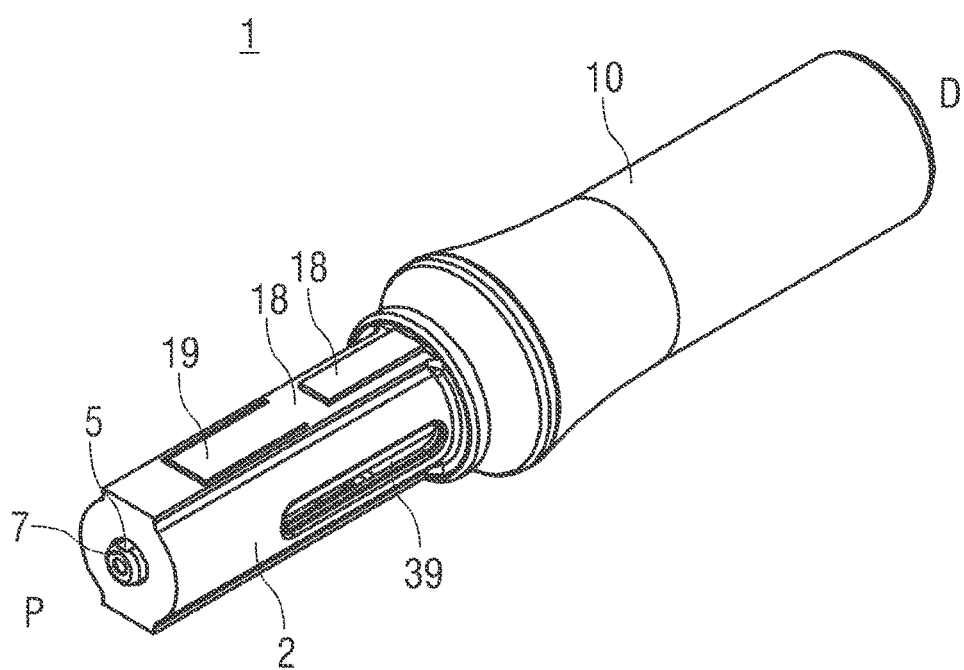
FIG. 1 is an isometric view of an embodiment of an auto-injector with a wrap-over sleeve trigger.

FIG. 1 shows an isometric view of an embodiment of an auto-injector 1 with a wrap-over sleeve trigger 10.

Figure 2:
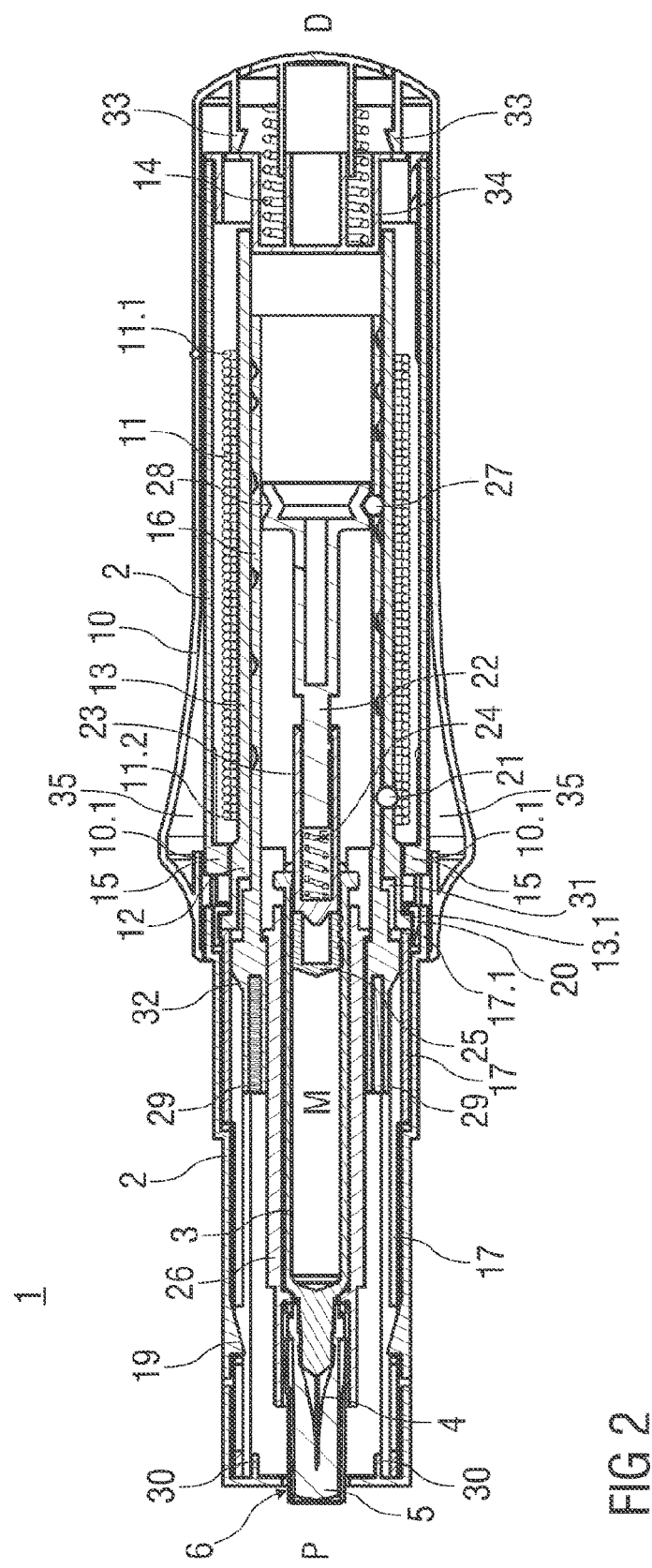
FIG. 2 is a longitudinal section of the auto-injector in an initial state.

FIG. 2 is a longitudinal section of the auto-injector 1 in an initial state. The auto-injector 1 comprises an elongate body 2. A syringe 3 with a hollow injection needle 4 is arranged in a proximal part of the auto-injector 1. When the auto-injector 1 is assembled a protective needle shield 5 is attached to the needle 4 and protruding through an orifice 6 at a proximal end P. A finger guard 7 in the shape of a sheet metal spring is arranged near the protective needle shield 5. The finger guard 7 is shown in detail in FIGS. 13 and 14. The finger guard 7 comprises two spring arms 8 which are inwardly biased so they bear against the protective needle shield 5 as long as it is still in place. A respective locking arm 9 is assigned to each spring arm 8. The locking arms 9 are biased in distal direction D so they bear against a part of the spring arms 8 when the protective needle shield 5 is in place. As the protective needle shield 5 is pulled away from the needle 4 (see FIG. 14) the spring arms 8 move inwards and relax leaving a small gap between them just wide enough to let the needle 4 pass without touching it. This allows the locking arms 9 to come clear of the spring arms 8 and move distally into a position where they prevent the spring arms 8 from being pushed outward again so despite the rather big orifice 6 the user cannot touch the tip of the needle 4. The tips of the spring arms 8 where the spring arms 8 bear against the protective needle shield 5 are rounded off in order to facilitate removal of the protective needle shield 5.

In alternative embodiments the spring arms 8 and/or the locking arms 9 may be made of or comprise spring wire and/or plastic instead of sheet metal. The spring arms 8 and locking arms 9 may be integrally formed as illustrated. They may also be separate parts, e.g. attached to inner walls of the proximal part of the auto-injector 1.

Figure 13:
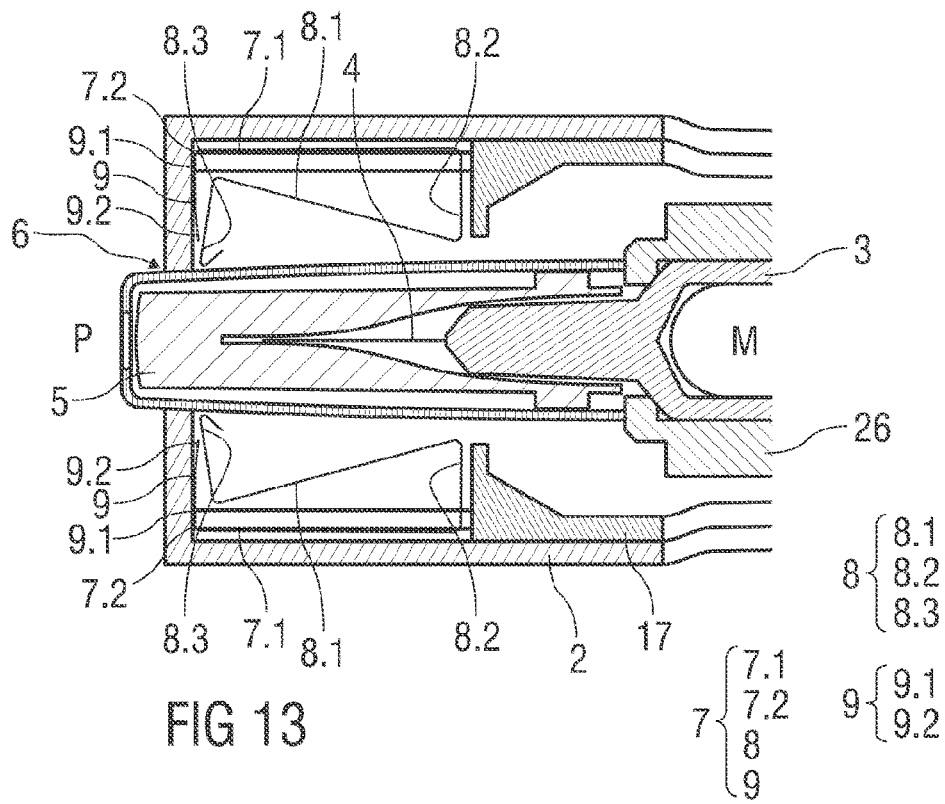
FIG. 13 is a detail view of a finger guard prior to use.
Figure 14:
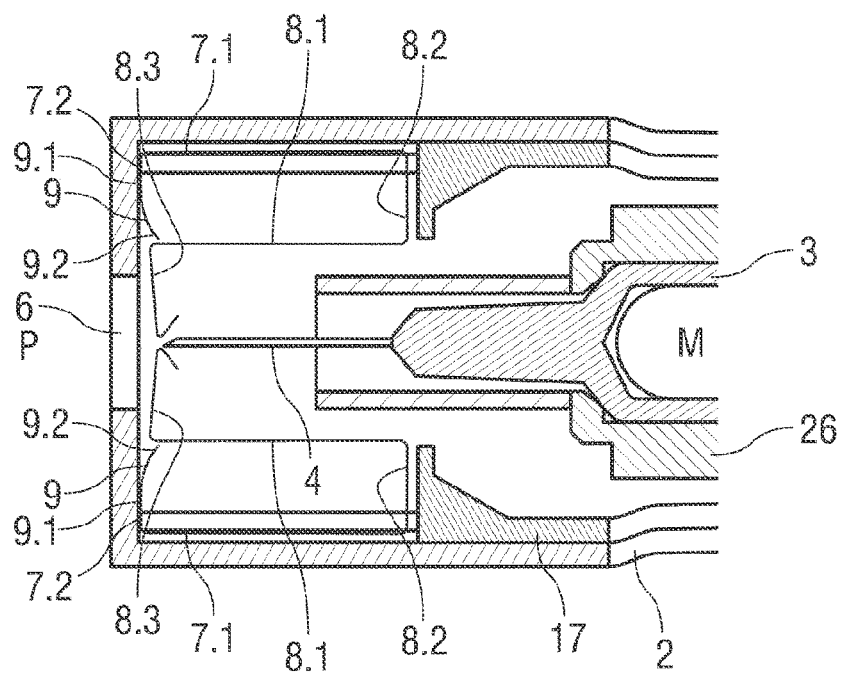
FIG. 14 is a detail view of the finger guard after removal of a protective needle shield.

Referring now to FIGS. 13 and 14, the spring arms 8 are essentially S-shaped with a longitudinal leg 8.1 in the middle and two transversal legs 8.2, 8.3 adjoining the longitudinal leg 8.1. When the spring arm 8 is relaxed, the transversal legs 8.2, 8.3 are essentially parallel to each other. An outer transversal leg 8.2 of each spring arm 8 adjoins a wall portion 7.1 of the sheet metal spring 7. The other, inner transversal 8.3 leg of each spring arm 8 is intended to bear against the protective needle shield 5. When the protective needle shield 5 is removed, a small gap is defined between the two inner transversal legs 8.3 of the spring arms 8. The locking arm 9 is a short arm with an outer end 9.1 adjoining a front portion 7.2 of the sheet metal spring 7 and with an inner end 9.2 bearing against the inner transversal leg 8.3 in distal direction D when the protective needle shield 5 is in place. When the protective needle shield 5 is removed the spring arms 8 move together and the locking arms 9 come clear of the inner transversal leg 8.3 when the joint between the inner transversal leg 8.3 and the longitudinal leg 8.1 passes the inner end 9.2. The inner end 9.2 locks behind the longitudinal leg 8.1 thus preventing the spring arm 8 from being pushed outward again. The tips of the spring arms' 8 inner transversal legs 8.3 where the spring arms 8 bear against the protective needle shield 5 are rounded off in order to facilitate removal of the protective needle shield 5.

The trigger sleeve 10 is arranged over the distal end D of the auto-injector 1 extending approximately over half the length of the auto-injector 1. In the initial state the trigger sleeve 10 is in a distal position. The trigger sleeve 10 may be translated into a proximal position relative to the body 2 against the bias of a trigger spring 14 arranged at the distal end D thus releasing a torsion spring 11 for starting an injection cycle.

Figure 3:
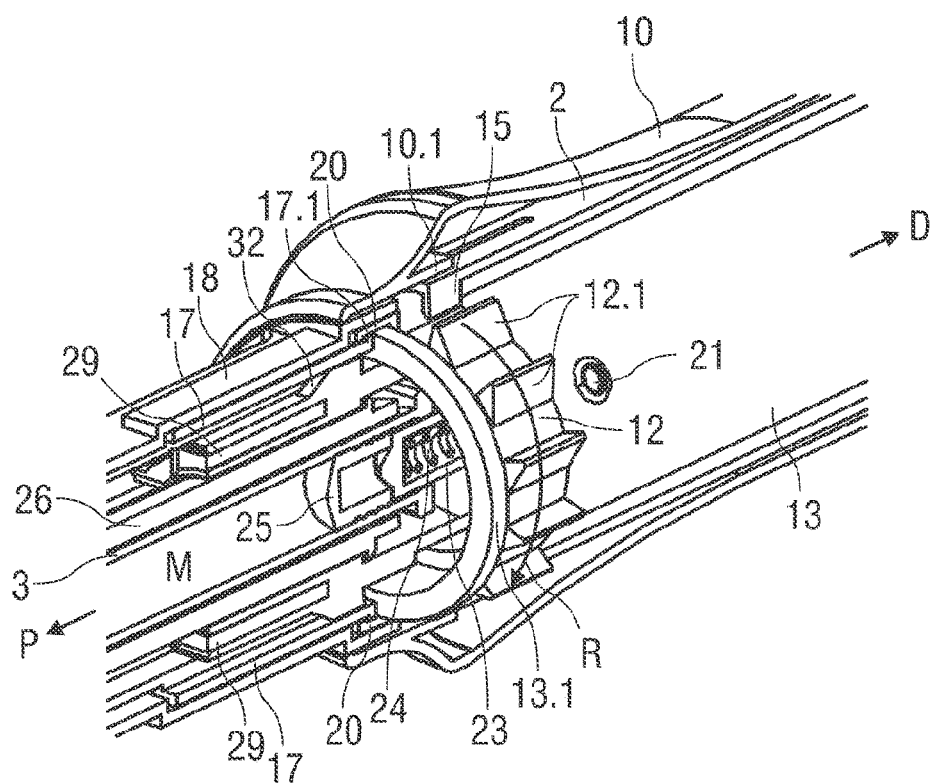
FIG. 3 is an isometric detail view of a trigger ratchet in the initial state.
Figure 4:
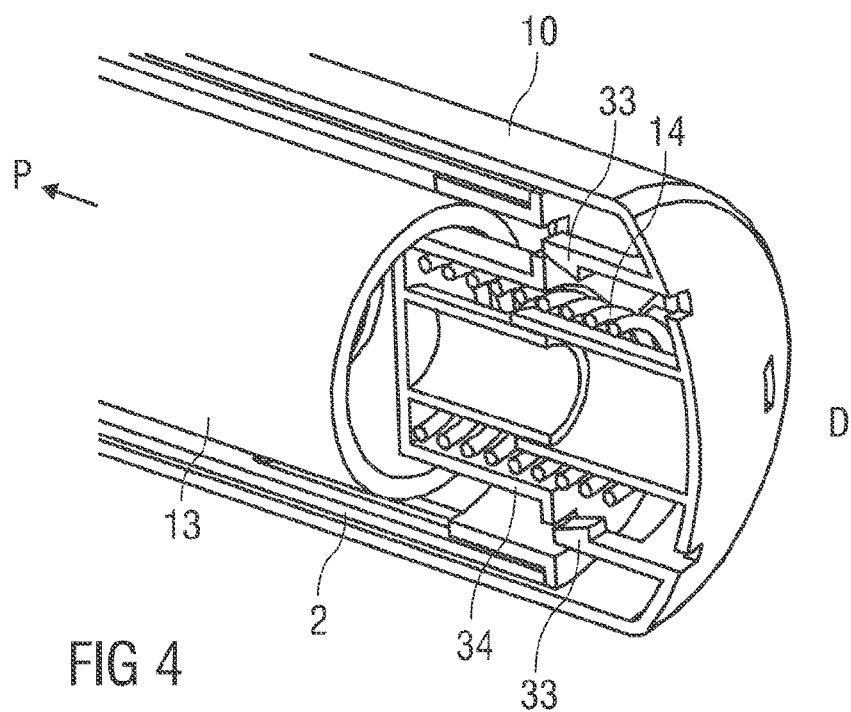
FIG. 4 is an isometric detail view of a distal end of the auto-injector in the initial state.

The torsion spring 11 is arranged inside the body 2 and grounded with its distal end 11.1 in the body 2 (cf. FIG. 2). The proximal end 11.2 of the torsion spring 11 is grounded in a follower tube 13 arranged inside the torsion spring 11 and rotatable with respect to the body 2. The torque from the proximal end 11.2 of the torsion spring 11 is resolved through a ratchet mechanism comprising a ratchet wheel 12 on the follower tube 13. The ratchet wheel 12 has a number of circumferentially arranged ramped teeth 12.1 with their ramps pointing towards a direction of rotation R of the follower tube 13 (see FIG. 3). Two resilient cantilever clips 15 are arranged on the body 2 in a position to be forced outward by the teeth 12.1 of the rotating ratchet wheel 12. In the initial state (cf. FIG. 3) however the cantilever clips 15 cannot move because they are constrained by respective stops 10.1 on the trigger sleeve 10. The torque from the torsion spring 11 is thus fully resolved in the initial state.

The follower tube 13 is telescoped with a lead screw tube 16. The lead screw tube 16 is supported and guided in a retraction slider tube 17 arranged in the proximal part of the body 2 in a manner to prevent the lead screw tube 16 from rotating while allowing it to be moved axially in proximal direction P. The retraction slider tube 17 in turn is engaged with the body 2 by flats 18 and latches 19 in a manner to prevent both rotation and translation with respect to the body 2 at least in the initial state shown in FIGS. 1 and 2. It will be shown in the following how the retraction slider tube 17 is disengaged from the latches 19 for being axially moved. The retraction slider tube 17 and the follower tube 13 are provided with respective first and second shoulders 17.1, 13.1 held together by a coupling ring 20 for allowing relative rotation but preventing them from being independently axially moved. The lead screw tube 16 has an external lead screw thread which is engaged with the follower tube 13 by one or more ball bearings 21. Rotation of the follower tube 13 therefore results in translation of the lead screw tube 16.

In the initial situation shown in FIG. 1 the retraction slider tube 17 can neither rotate nor move axially, the follower tube 13 cannot move axially and is prevented from rotating by the ratchet wheel 12 engaged with the cantilever clips 15. The lead screw tube 16 is prevented from rotation.

In order to prepare for an injection the user removes the protective needle shield 5 from the needle 4. For this purpose a device cap (not shown) may be attached to the protective needle shield 5. When the needles shield 5 is removed the finger guard 7 locks into place to protect the user from accidental needlestick injuries (cf. FIG. 14).

Figure 5:
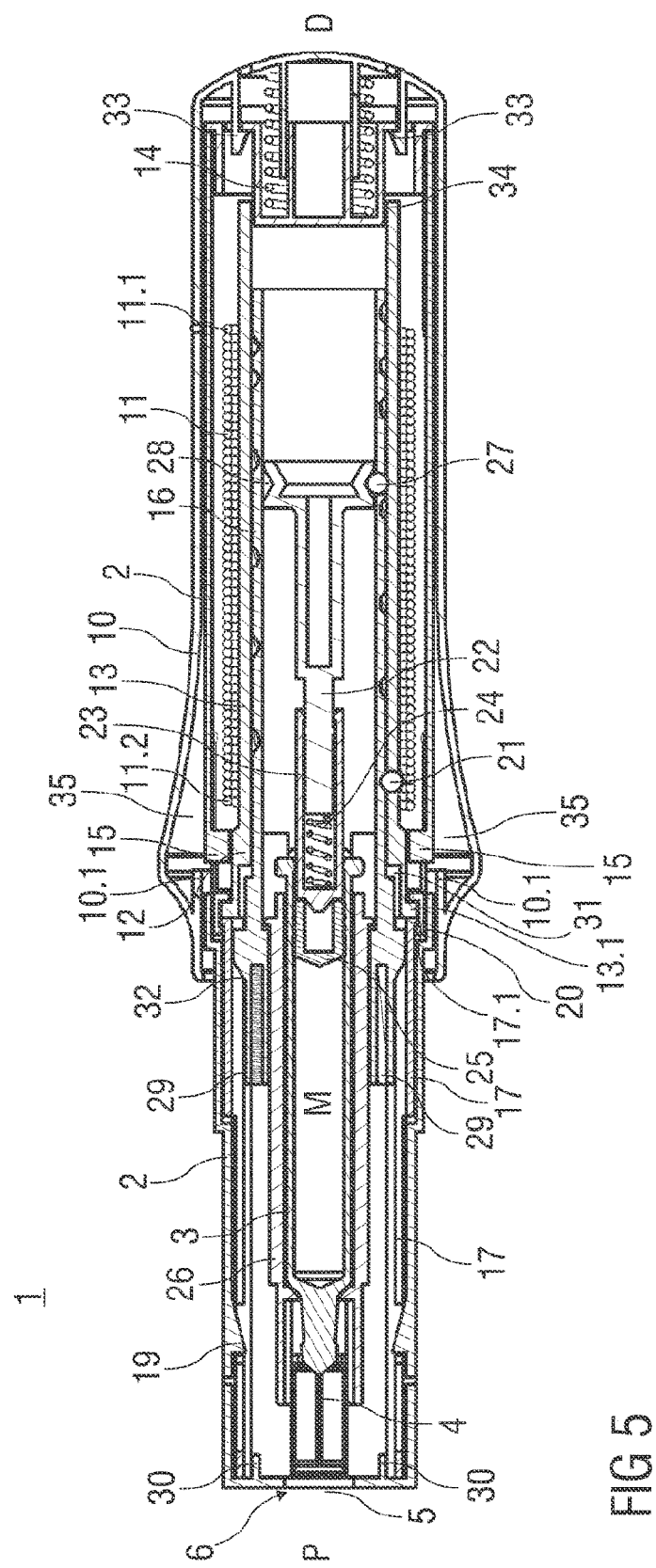
FIG. 5 is a longitudinal section of the auto-injector at a point of actuation.
Figure 6:
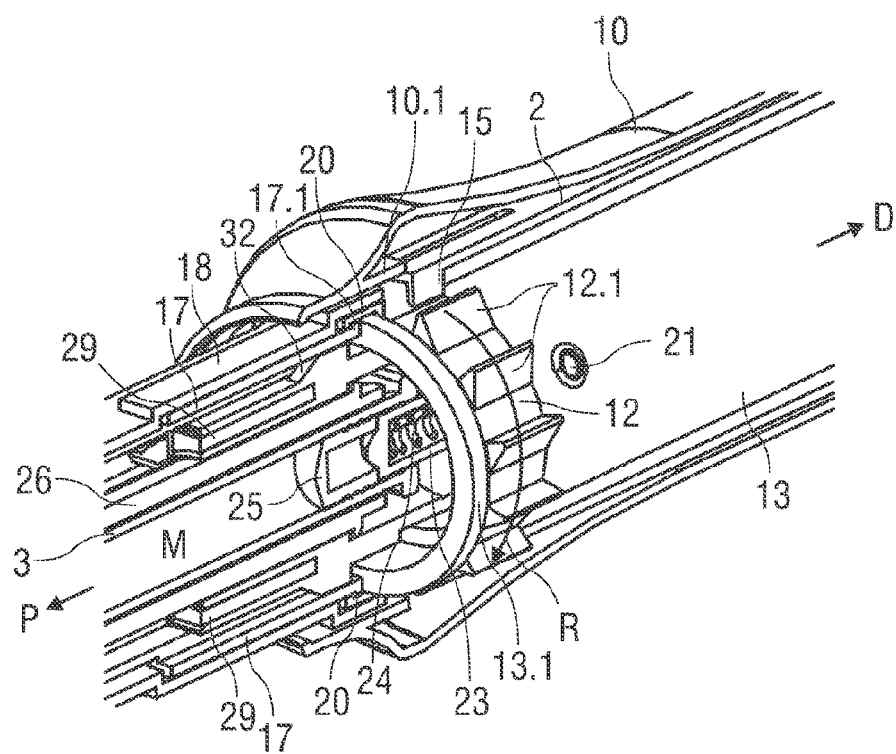
FIG. 6 is an isometric detail view of a trigger ratchet at the point of actuation.
Figure 7:
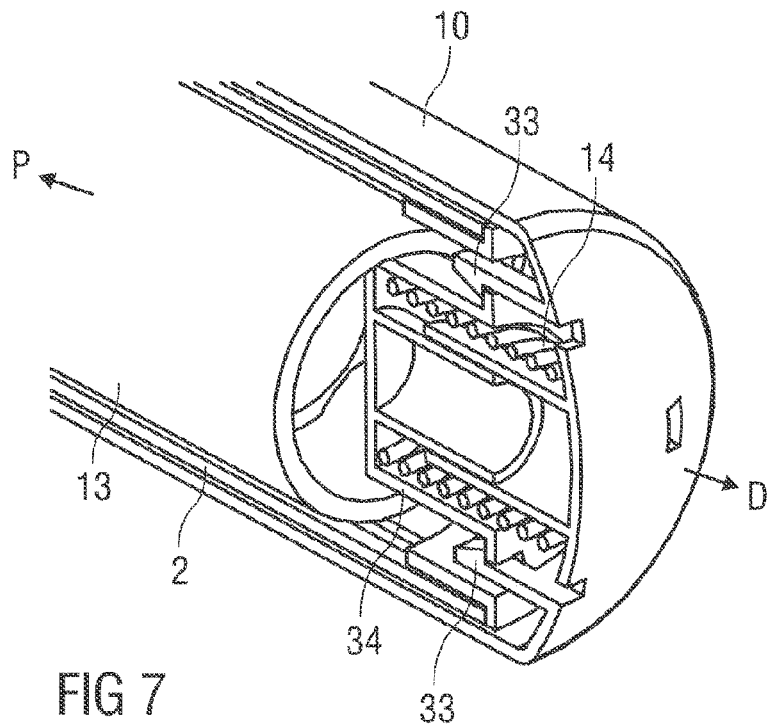
FIG. 7 is an isometric detail view of a distal end of the auto-injector at the point of actuation.

In order to start an injection the user grabs the trigger sleeve 10 with their hand, places the auto-injector 1 with the orifice 6 ahead on the injection site and pushes it firmly against the injection site while holding the trigger sleeve 10. The load applied causes the trigger sleeve 10 to translate in proximal direction P into the proximal position (see FIGS. 5, 6 and 7). The stops 10.1 on the trigger sleeve 10 are thus relocated so as to allow the cantilever clips 15 to be flexed outwards into recesses 35 in the trigger sleeve 10 by the teeth 12.1 of the ratchet wheel 12. This allows the follower tube 13 to rotate due to the torque of the torsion spring 11. Two clip features 33 at the distal end of the trigger sleeve 10 lock the trigger sleeve 10 in the proximal position to a spring boss 34 attached to the body 2 at the distal end D and arranged to accommodate the trigger spring 14. The clip features 33 may likewise be arranged in a different place between the trigger sleeve 10 and the body 2.

The rotation of the follower tube 13 causes translation of the lead screw tube 16 in proximal direction P. Inside the lead screw tube 16 a two part plunger with a plunger rear 22 and a plunger front 23 is arranged, the plunger rear 22 telescoped into the hollow plunger front 23. In the plunger front 23 a plunger spring 24 in the shape of a compression spring is arranged which bears against the plunger rear 22 when the plunger rear 22 pushed in proximal direction P. The plunger front 23 in turn pushes against a stopper 25 arranged for sealing the syringe 3 distally and for displacing a liquid medicament M through the hollow needle 4. The syringe is held in a tubular syringe carrier 26 and supported at its proximal end therein. The plunger rear 22 is coupled for joint axial translation to the lead screw tube 16 by a plunger ball 27 arranged in a recess in the lead screw tube 16 and guided in a circumferential notch 28 of the plunger rear 22. In the initial position shown in FIG. 2 the plunger ball 27 is held in position by the follower tube 13 in order to keep the plunger rear 22 and lead screw tube 16 from disengaging.

Consequently, when the lead screw tube 16 is advanced in proximal direction P the syringe 3 is driven forward by the plunger 22, 23 pushing on the stopper 25.

The external lead screw thread of the lead screw tube 16 has a variable pitch. In the embodiment shown in the figures the pitch is steeper in the proximal part of the external lead screw (cf. FIG. 2). This allows for a rapid insertion of the hollow needle 4 into the patient's skin in order to avoid unnecessary pain for the patient. The load required to insert a siliconized fine gauge needle is thought to be in the region of 5 N, which is relatively low so a steep screw pitch can be used with little risk of the screw engagement locking.

In case the screw engagement between the follower tube 13 and the lead screw tube 16 comprises more than one ball bearing 21 each ball 21 may be engaged with a respective screw thread so the lead screw tube 16 would have a multi-start thread.

At the end of needle insertion the syringe carrier 26 bottoms out at the proximal end P of the body 2 thus defining an injection depth, e.g. for a subcutaneous injection.

As the torsion spring 11 continues rotating the lead screw tube 16, and plunger rear 22 are further forwarded. Due to friction effective between the stopper 25 and the inner wall of the syringe 3 and due to the thin fluid channel inside the hollow needle 4 opposing the displacement of the medicament M the stopper 25 exerts a load against the forward movement of the plunger front 23. Thus, the plunger spring 24 is slightly compressed. The thrust load is reacted through the ball 27, lead screw tube 16, follower tube 13 and coupling ring 20 into the retraction slider tube 17 which is coupled to the body 2 by the latches 19. Thus the follower tube 13 is kept from moving in distal direction D. With continued forward movement of the plunger 22, 23 the stopper 25 is advanced and injects the medicament M from the syringe 3 into the injection site. During injection of the dose of medicament M the pitch of the lead screw thread is slightly reduced compared to the needle insertion in order to give a greater mechanical advantage to the lead screw engagement and avoid it stalling due to the increased load.

The cantilever clips 15 running over the teeth 12.1 of the ratchet wheel 12 will produce an audible and tactile feedback that the injection is in progress.

Towards the end of the dose, i.e. just before the stopper 25 bottoms out in the syringe 3 viscous dampers 29 contained in pockets in the proximal end of the lead screw tube 16 contact small ribs 30 in the proximal end P of the body 2. Thus load from the torsion spring 11 is shared between the stopper 25 and the contact between the ribs 30 and the viscous dampers 29, so the plunger spring 24 is allowed to extend and complete the dose by fully advancing the stopper 25. This allows for fully emptying the syringe 3 before starting to retract the needle 4.

The viscous damper 29 has a speed dependent load characteristic. In this instance the load from the torsion spring 11 is almost constant over the small axial travel of the viscous damper 29 so the speed can be tuned so that the plunger spring 24 has enough time to fully expel the residual contents of the syringe 3. The material of the viscous damper 29 may be viscoelastic foam or a fluid forced through a small orifice.

A change in the lead screw pitch at this point allows a controlled increase in the mechanical advantage to apply sufficient force to the mechanism.

When the stopper 25 has bottomed out in the syringe 3 the lead screw tube 16 reaches the end of travel. Just before this the plunger ball 27 disengages the plunger rear 22 from the lead screw tube 16 by dropping out of its recess into a pocket 31 in the follower tube 13. Just after this the latches 19 are released by ramp features 32 of the lead screw tube 16 pushing them outward so the retraction slider tube 17 and the follower tube 13 are released from the body 2 with respect to translation. Since the lead screw tube 16 has bottomed out at the proximal end P of the body 2 continued rotation of the torsion spring 11 results in a backward movement of the retraction slider tube 17 and the follower tube 13 which is still rotating. The retraction slider tube 17 takes along the syringe carrier 26 and retracts it into the auto-injector 1 until the hollow needle 4 is fully covered. For this purpose the retraction slider tube 17 may have one or more dog features extending inwardly through recesses in the lead screw tube 16 and engaging the syringe carrier 26 (dog features not illustrated).

A viewing window 39 is provided for inspecting the syringe contents.

In FIGS. 3, 4, 6 and 7 the torsion spring 11 is not shown for clarity.

Figure 8:
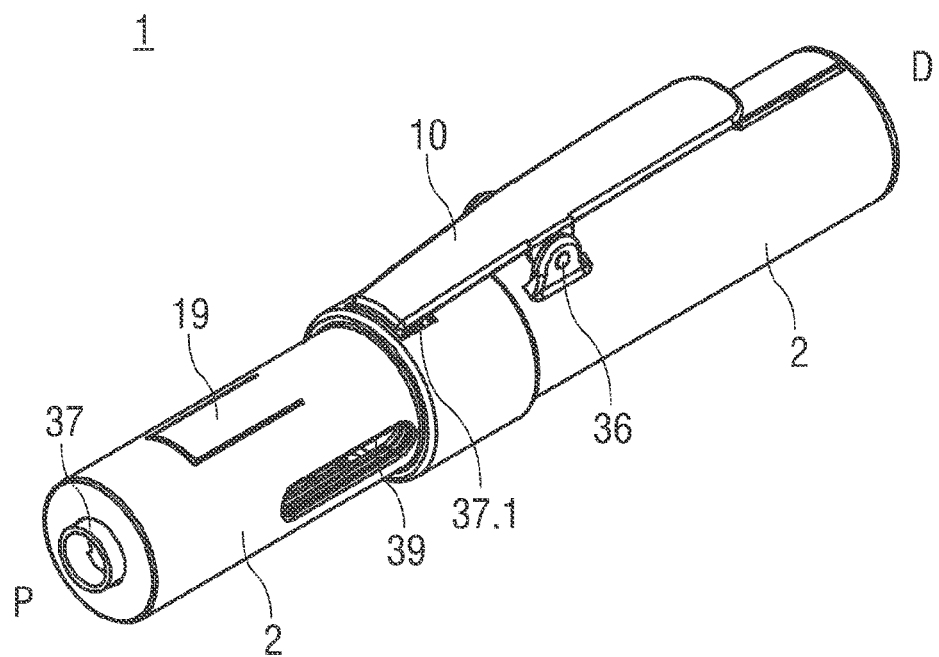
FIG. 8 is an isometric view of another embodiment of an auto-injector with a lateral trigger button.

FIG. 8 shows an isometric view of another embodiment of an auto-injector 1 with a laterally arranged trigger button 10 instead of the wrap-over sleeve trigger 10.

Figure 9:
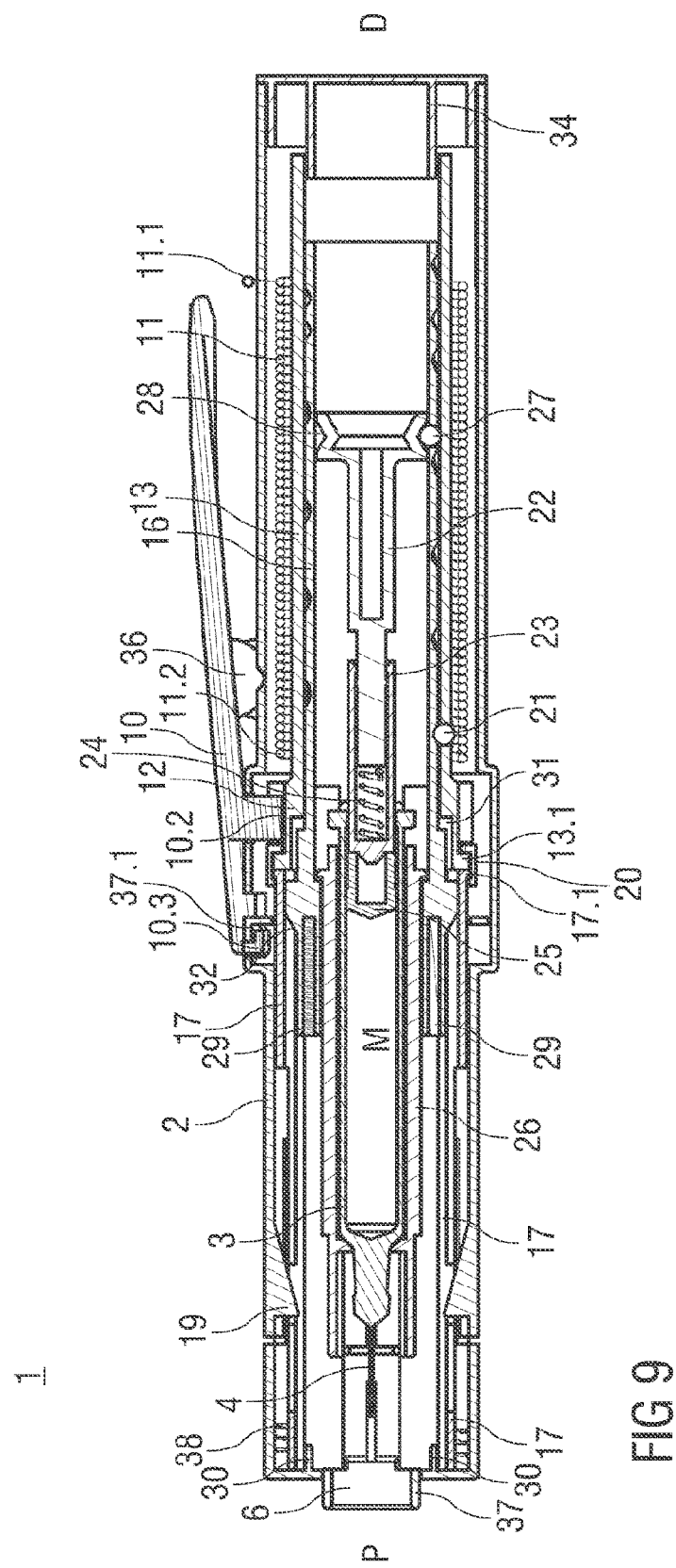
FIG. 9 is a longitudinal section of the auto-injector of FIG. 8 in the initial state.

FIG. 9 is a longitudinal section of the auto-injector 1 in an initial state. The auto-injector 1 comprises an elongate body 2. A syringe 3 with a hollow injection needle 4 is arranged in a proximal part of the auto-injector 1. A protective needle shield and a finger guard similar to the embodiment in FIGS. 1 to 7 may be arranged.

Figure 10:
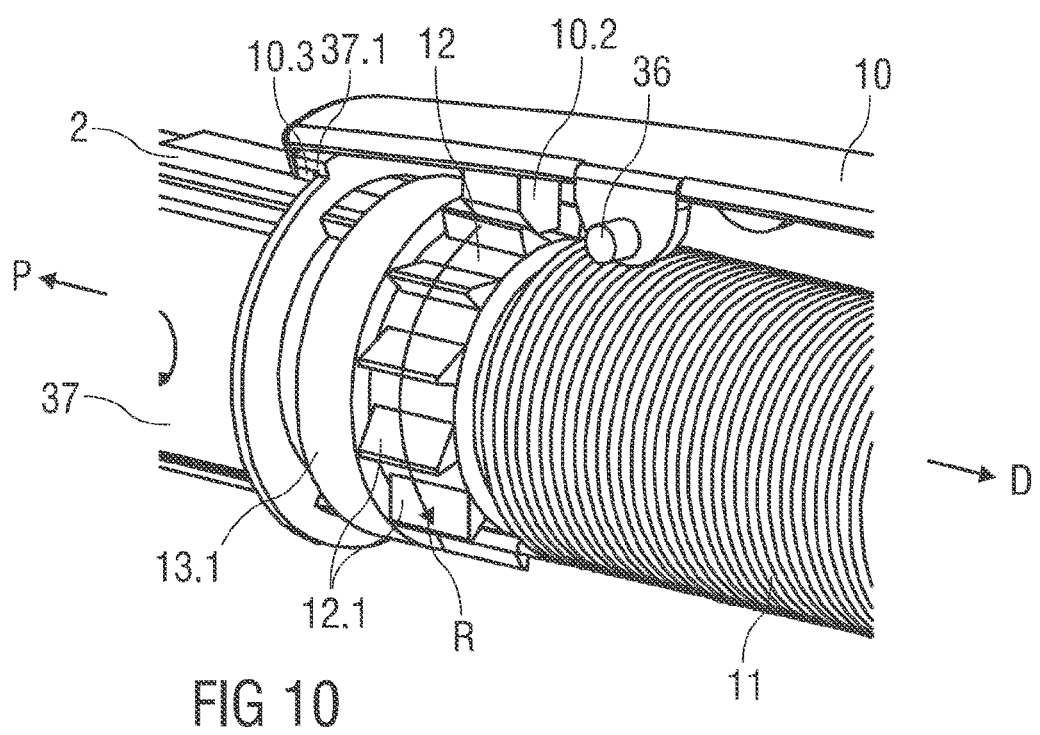
FIG. 10 is an isometric detail view of a trigger ratchet of the auto-injector of FIG. 8 in the initial state.

The rocker type trigger button 10 is laterally arranged on the body 2 and pivoted about a trigger pivot 36 in the body 2. In the initial state a tooth 10.2 on the trigger button 10 proximally from the trigger pivot 36 is engaged with teeth 12.1 of a ratchet wheel 12 on the follower tube 13 (see FIG. 10). A catch 10.3 on the proximal end of the trigger button 10 is engaged to a catch 37.1 on a distal end of an interlock sleeve 37 arranged in the proximal part of the body 2 in a manner to protrude from the proximal end P of the body 2 in the initial state under bias of an interlock spring 38. The interlock sleeve 37 is translatable in distal direction D into a distal position against the load of the interlock spring 38 by pushing the proximal end P against an injection site thereby also translating the catch 37.1 and disengaging it from the catch 10.3. When the catches 10.3, 37.1 are engaged the trigger button 10 is prevented from being operated. Disengaging the catches 10.3, 37.1 releases the trigger button 10 for being operated. Operating the trigger button 10 disengages the tooth 10.2 from the teeth 12.1 thus releasing the torsion spring 11 for starting an injection cycle.

The torsion spring 11 is arranged inside the body 2 and grounded with its distal end 11.1 in the body 2. The proximal end 11.2 of the torsion spring 11 is grounded in the follower tube 13 arranged inside the torsion spring 11 and rotatable with respect to the body 2. The torque from the proximal end 11.2 of the torsion spring 11 is resolved through the ratchet mechanism comprising the ratchet wheel 12 on the follower tube 13 and the tooth 10.2 of the trigger button 10. The ratchet wheel 12 has a number of circumferentially arranged ramped teeth 12.1 with their ramps pointing against a direction of rotation R of the follower tube 13 (see FIG. 10). In the initial state the torque from the proximal end 11.2 of the torsion spring 11 is resolved through the ratchet wheel 12, the tooth 10.2, the trigger button 10 and the pivot 36 into the body 2.

The follower tube 13 is telescoped with a lead screw tube 16. The lead screw tube 16 is supported and guided in a retraction slider tube 17 arranged in the proximal part of the body 2 in a manner to prevent the lead screw tube 16 from rotating while allowing it to be moved axially in proximal direction P. The retraction slider tube 17 in turn is engaged with the body 2 by flats (not illustrated, similar to the other embodiment) and latches 19 in a manner to prevent both rotation and translation with respect to the body 2 at least in the initial state shown in FIG. 9. It will be shown in the following how the retraction slider tube 17 is disengaged from the latches 19 for being axially moved. The retraction slider tube 17 and the follower tube 13 are provided with respective first and second shoulders 17.1, 13.1 held together by a coupling ring 20 for allowing relative rotation but preventing them from being independently axially moved. The lead screw tube 16 has an external lead screw thread which is engaged with the follower tube 13 by one or more ball bearings 21. Rotation of the follower tube 13 therefore results in translation of the lead screw tube 16.

In the initial situation shown in FIG. 9 the retraction slider tube 17 can neither rotate nor move axially, the follower tube 13 cannot move axially and is prevented from rotating by the ratchet wheel 12 engaged with the tooth 10.2. The lead screw tube 16 is prevented from rotation.

In order to prepare for an injection the user may have to remove a protective needle shield from the needle (not illustrated).

Figure 11:
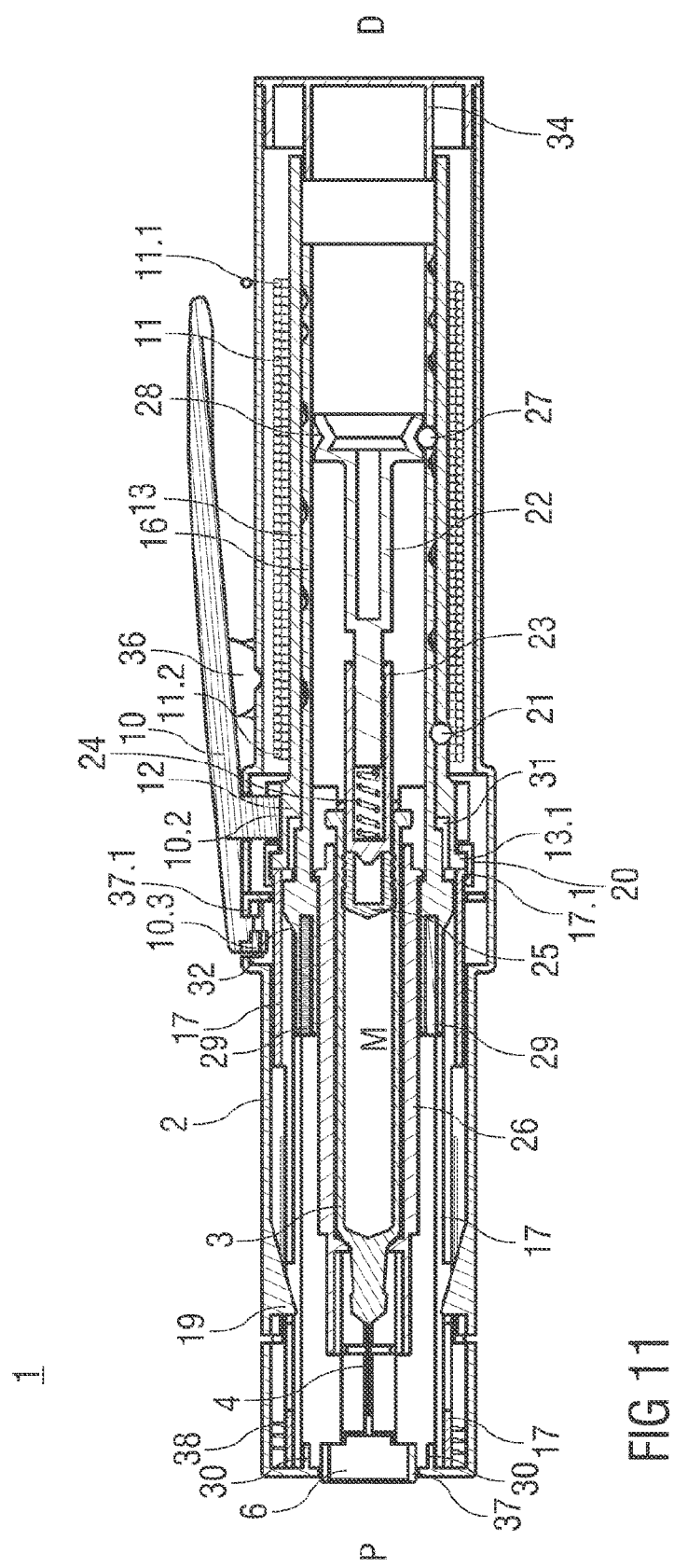
FIG. 11 is a longitudinal section of the auto-injector of FIG. 8 with a skin interlock depressed.

In order to start an injection the user positions the auto-injector 1 with the orifice 6 aligned with the injection site and pushes it firmly against the injection site. The load applied causes the interlock sleeve 37 to translate in distal direction D into the distal position (see FIG. 11) against the bias of the interlock spring 38. The catch 37.1 on the interlock sleeve 37 is thus relocated so as to disengage from the catch 10.3 on the trigger button 10 thus releasing the trigger button 10 for operation.

Figure 12:
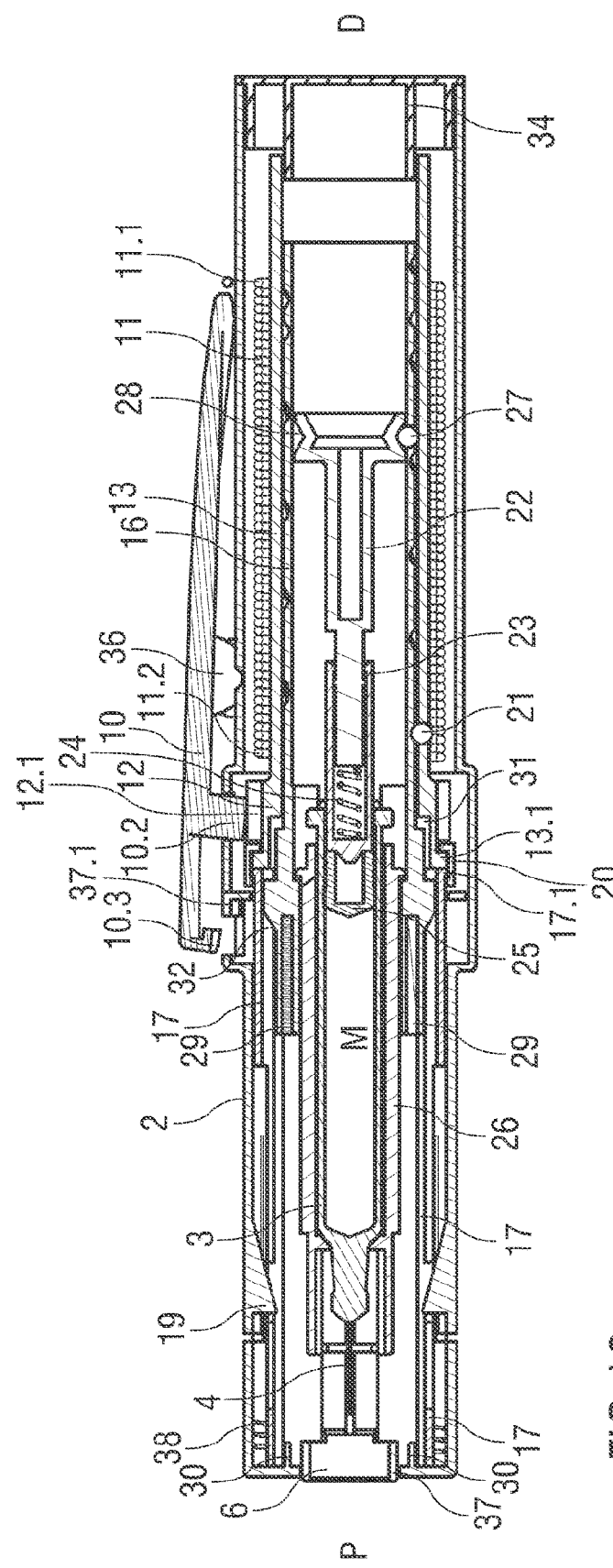
FIG. 12 is a longitudinal section of the auto-injector of FIG. 8 at the point of actuation of the trigger button.

The user may now depress the distal end of the trigger button 10 which rotates around the pivot 36, disengaging the tooth 10.2 from the ratchet wheel teeth 12.1 (see FIG. 12).

This allows the follower tube 13 to rotate due to the torque of the torsion spring 11.

The rotation of the follower tube 13 causes translation of the lead screw tube 16 in proximal direction P. Inside the lead screw tube 16 a two part plunger with a plunger rear 22 and a plunger front 23 is arranged, the plunger rear 22 telescoped into the hollow plunger front 23. In the plunger front 23 a plunger spring 24 in the shape of a compression spring is arranged which bears against the plunger rear 22 when the plunger rear 22 is pushed in proximal direction P. The plunger front 23 in turn pushes against a stopper 25 arranged for sealing the syringe 3 distally and for displacing a liquid medicament M through the hollow needle 4. The syringe is held in a tubular syringe carrier 26 and supported at its proximal end therein. The plunger rear 22 is coupled for joint axial translation to the lead screw tube 16 by a plunger ball 27 arranged in a recess in the lead screw tube 16 and guided in a circumferential notch 28 of the plunger rear 22. In the initial position shown in FIG. 8 the plunger ball 27 is held in position by the follower tube 13 in order to keep the plunger rear 22 and lead screw tube 16 from disengaging.

When the lead screw tube 16 is advanced in proximal direction P the syringe 3 is driven forward by the plunger 22, 23 pushing on the stopper 25.

The external lead screw thread of the lead screw tube 16 has a variable pitch. In the embodiment shown in the figures the pitch is steeper in the proximal part of the external lead screw (cf. FIG. 9). This allows for a rapid insertion of the hollow needle 4 into the patient's skin in order to avoid unnecessary pain for the patient. The load required to insert a siliconized fine gauge needle is thought to be in the region of 5 N, which is relatively low so a steep screw pitch can be used with little risk of the screw engagement locking.

In case the screw engagement between the follower tube 13 and the lead screw tube 16 comprises more than one ball bearing 21 each ball 21 may be engaged with a respective screw thread so the lead screw tube 16 would have a multi-start thread.

At the end of needle insertion the syringe carrier 26 bottoms out at the proximal end P of the body 2 thus defining an injection depth, e.g. for a subcutaneous injection.

As the torsion spring 11 continues rotating the lead screw tube 16, and plunger rear 22 are further forwarded. Due to friction effective between the stopper 25 and the inner wall of the syringe 3 and due to the thin fluid channel inside the hollow needle 4 opposing the displacement of the medicament M the stopper 25 exerts a load against the forward movement of the plunger front 23. Thus, the plunger spring 24 is slightly compressed. The thrust load is reacted through the ball 27, lead screw tube 16, follower tube 13 and coupling ring 20 into the retraction slider tube 17 which is coupled to the body 2 by the latches 19. Thus the follower tube 13 is kept from moving in distal direction D. With continued forward movement of the plunger 22, 23 the stopper 25 is advanced and injects the medicament M from the syringe 3 into the injection site. During injection of the dose of medicament M the pitch of the lead screw is slightly reduced compared to the needle insertion in order to give a greater mechanical advantage to the lead screw engagement and avoid it stalling due to the increased load.

Towards the end of the dose, i.e. just before the stopper 25 bottoms out in the syringe 3 viscous dampers 29 contained in pockets in the proximal end of the lead screw tube 16 contact small ribs 30 in the proximal end P of the body 2. Thus load from the torsion spring 11 is shared between the stopper 25 and the contact between the ribs 30 and the viscous dampers 29, so the plunger spring 24 is allowed to extend and complete the dose by fully advancing the stopper 25. This allows for fully emptying the syringe 3 before starting to retract the needle 4.

The viscous damper 29 has a speed dependent load characteristic. In this instance the load from the torsion spring 11 is almost constant over the small axial travel of the viscous damper 29 so the speed can be tuned so that the plunger spring 24 has enough time to fully expel the residual contents of the syringe 3. The material of the viscous damper 29 may be viscoelastic foam or a fluid forced through a small orifice.

A change in the lead screw pitch at this point allows a controlled increase in the mechanical advantage to apply sufficient force to the mechanism.

When the stopper 25 has bottomed out in the syringe 3 the lead screw tube 16 reaches the end of travel. Just before this the plunger ball 27 disengages the plunger rear 22 from the lead screw tube 16 by dropping out of its recess into a pocket 31 in the follower tube 13. Just after this the latches 19 are released by ramp features 32 of the lead screw tube 16 pushing them outward so the retraction slider tube 17 and the follower tube 13 are released from the body 2 with respect to translation. Since the lead screw tube 16 has bottomed out at the proximal end P of the body 2 continued rotation of the torsion spring 11 results in a backward movement of the retraction slider tube 17 and the follower tube 13 which is still rotating. The retraction slider tube 17 takes along the syringe carrier 26 and retracts it into the auto-injector 1 until the hollow needle 4 is fully covered. For this purpose the retraction slider tube 17 may have one or more dog features extending inwardly through recesses in the lead screw tube 16 and engaging the syringe carrier 26 (dog features not illustrated).

A viewing window 39 is provided for inspecting the syringe contents.

The auto-injector 1 of either embodiment may preferably be used for subcutaneous or intra-muscular injection, particularly for delivering one of an analgetic, an anticoagulant, insulin, an insulin derivate, heparin, Lovenox, a vaccine, a growth hormone, a peptide hormone, a protein, antibodies and complex carbohydrates.

The invention claimed is:

1. Auto-injector for administering a dose of a liquid medicament (M), comprising:
    a body arranged to contain a syringe with a hollow injection needle and a stopper for sealing the syringe and displacing the medicament (M), the body having a distal end (D) and a proximal end (P) with an orifice intended to be applied against an injection site, wherein the syringe is slidably arranged with respect to the body;
    a torsion spring capable of, upon activation:
        pushing the needle from a covered position inside the body into an advanced position through the orifice and past the proximal end (P),
        operating the syringe to supply the dose of medicament (M); and
    an activating mechanism comprising either a wrap-over trigger sleeve or a trigger button, the activating mechanism arranged to lock the torsion spring in a pressurized state prior to manual operation and capable of, upon manual operation, releasing the torsion spring for injection;
    wherein the torsion spring is grounded at one end in the body and at the other end in a first gear member rotatable about a longitudinal axis, wherein the first gear member, upon rotation, is arranged for translating a second gear member toward the proximal end (P), the second gear member prevented from rotating and arranged to be coupled to the stopper in order to push it towards the proximal end (P), wherein the first gear member is engaged with the activating mechanism prior to manual operation in a manner to prevent rotation and disengaged from the activating mechanism upon manual operation;
    wherein a ratchet wheel is arranged on the first gear member, the ratchet wheel having a number of circumferentially arranged teeth, wherein the activating mechanism comprises at least one locking feature for engaging the ratchet wheel in a manner to prevent rotation and wherein the locking feature is arranged to allow rotation on manual operation.

2. Auto-injector according to claim 1, wherein the activating mechanism comprises the wrap-over trigger sleeve arranged over the distal end (D) of the auto-injector and translatable between a distal position and a proximal position, wherein the trigger sleeve is biased in distal direction (D), wherein the locking feature is at least one resilient cantilever clip arranged on the body in a position to be forced outward by the ramped teeth of the rotating ratchet wheel with their ramps pointing towards a direction of rotation (R) of the first gear member, wherein the trigger sleeve comprises at least one stop for outwardly supporting the cantilever clip when the trigger sleeve is in the distal position, wherein the stop is arranged to be removed from behind the cantilever clip on translation of the trigger sleeve into the proximal position.

3. Auto-injector according to claim 1, wherein the activating mechanism comprises the trigger button laterally arranged on the body and pivoted about a trigger pivot in the body, wherein the locking feature is a tooth arranged on the trigger button, wherein the tooth is engaged with the ratchet wheel in an initial state prior to actuation of the trigger button, wherein the tooth is arranged to be moved outwards and disengaged from the ratchet wheel on actuation of the trigger button.

4. Auto-injector according to claim 3, wherein an interlock sleeve is arranged in the proximal part of the body in a manner to protrude from the proximal end (P) in the initial state under bias of an interlock spring, wherein the interlock sleeve is translatable in distal direction (D) into a distal position against the load of the interlock spring by pushing the proximal end (P) against an injection site, wherein a catch is arranged on the interlock sleeve in a manner to engage a catch on the trigger button so as to prevent the trigger button from being operated when the interlock sleeve is in the proximal position, wherein the catches are arranged to be disengaged on translation of the interlock sleeve into the distal position.

5. Auto-injector according to claim 3, wherein the trigger button is biased so as to reengage the tooth with the ratchet wheel for interrupting rotation of the first gear member.

6. Auto-injector according to claim 5, wherein the ratchet wheel comprises circumferentially arranged ramped teeth with their ramps pointing against a direction of rotation (R) of the first gear member.

7. Auto-injector according to claim 1, wherein a retraction slider tube is arranged in a proximal part of the body in a manner to be prevented from rotation and wherein at least one latch for restricting axial translation of the retraction slider tube is provided in the body, the latch being disengageable by at least one ramp feature on the second gear member when the second gear member is in or near a maximum proximal position, wherein the retraction slider tube comprises at least one dog feature for retracting the syringe when the retraction slider tube is retracted by the first gear member.

8. Auto-injector according to claim 7, wherein the first gear member is coupled to the retraction slider tube for joint axial translation but independent rotation.

9. Auto-injector according to claim 1, wherein the first gear member is a follower tube and that the second gear member is a lead screw tube, wherein the lead screw tube is telescoped in the follower tube, wherein the lead screw tube has a lead screw thread engaged with the follower tube by at least one ball bearing.

10. Auto-injector according to claim 9, wherein the syringe is held in an essentially tubular syringe carrier and supported at its proximal end therein, wherein the syringe carrier is slidably arranged in the lead screw tube, wherein the dog feature is arranged for engaging the syringe carrier for retraction of the syringe.

11. Auto-injector according to claim 9, wherein the lead screw thread has a variable pitch arranged in a manner to advance the lead screw tube faster and with less force when inserting the hollow needle and more slowly with increased force when expelling the medicament (M).

12. Auto-injector according to claim 1, wherein the second gear member is coupled to the stopper by a plunger which is releasably engageable with the second gear member for joint axial movement, wherein the plunger is disengageable from the second gear member upon the second gear member reaching its maximum proximal position.

13. Auto-injector according to claim 12, the plunger is engageable with the second gear member by at least one plunger ball detent, wherein the ball detent is supported by the first gear member when engaged and wherein the plunger is disengageable by the ball detent reaching a pocket in the first gear member and the detent ball dropping into the pocket.

14. Auto-injector according to claim 12, wherein the plunger comprises a plunger rear and a plunger front telescoped into each other, wherein a plunger spring is arranged between the plunger rear and plunger front, wherein the plunger spring is arranged for being partially compressed when the plunger is being advanced to push the stopper towards the proximal end (P).

15. Auto-injector according to claim 14, wherein the second gear member is provided with pockets containing a respective viscous damper at the proximal end of the second gear member the viscous damper arranged for being compressed by a respective rib arranged in the proximal end of the body when the second gear member nearly reaches a maximum proximal position thereby resolving part of the load from the second gear member and allowing the plunger spring to expand.

* * * * *